July 8, 1958

F. W. ANDERSON

Plant Pat. 1,724

NECTARINE TREE

Filed Oct. 29, 1957

WITNESS

Addison E. Avery

INVENTOR

Frederic W. Anderson

Deistler & Deistler

ATTYS.

United States Patent Office

Plant Pat. 1,724
Patented July 8, 1958

1,724

NECTARINE TREE

Frederic W. Anderson, Merced, Calif., assignor to The Burchell Nursery, Modesto, Calif.

Application October 29, 1957, Serial No. 693,222

1 Claim. (Cl. 47—62)

This invention is directed to a new and distinct variety of nectarine tree that bears large, firm, yellow fleshed, freestone fruit, characterized by a relatively late ripening period, capable of well withstanding long-distance shipment, and of very acceptable market quality.

This new and distinct variety of nectarine tree was originated by me in my experimental nursery and orchard, located near Merced, California, as a first generation (F-1) seedling of a Le Grand nectarine (United States Plant Patent No. 549) × Royal Hale Peach (United States Plant Patent No. 1,247).

Seeds of such cross were planted, and the resultant seedlings were subsequently brought into bearing under conditions of careful observation; it having been noted that of such resultant seedlings approximately one-half were peaches and one-half nectarines. Of such nectarine trees, which bore freestone fruit, the most promising were selected for propagation and were budded, in my orchard located as aforesaid, onto mature orchard trees, along with certain well recognized commercial nectarine varieties, in order that an effective comparison could be made.

Of such selected and budded nectarines the instant variety appeared to offer greater commercial possibilities, by reason of the aforementioned relatively late ripening period, and other characteristics which herein appear.

Subsequently, the variety has been further asexually reproduced—in my orchard—in like manner and has been found to carry forward all of the characteristics of the parent tree.

In comparison with the Freedom nectarine (United States Plant Patent No. 1,161) the fruit of the present variety ripens aprpoximately ten days to two weeks later, thus correspondingly and desirably extending the market period; the fruit here being somewhat larger in size and firmer of flesh, with a longer keeping quality.

In comparison with the Golden Grand nectarine (United States Plant Patent No. 1,324) the fruit of the present variety is more uniform in size, somewhat firmer of flesh, and of better eating quality.

Figure 1:
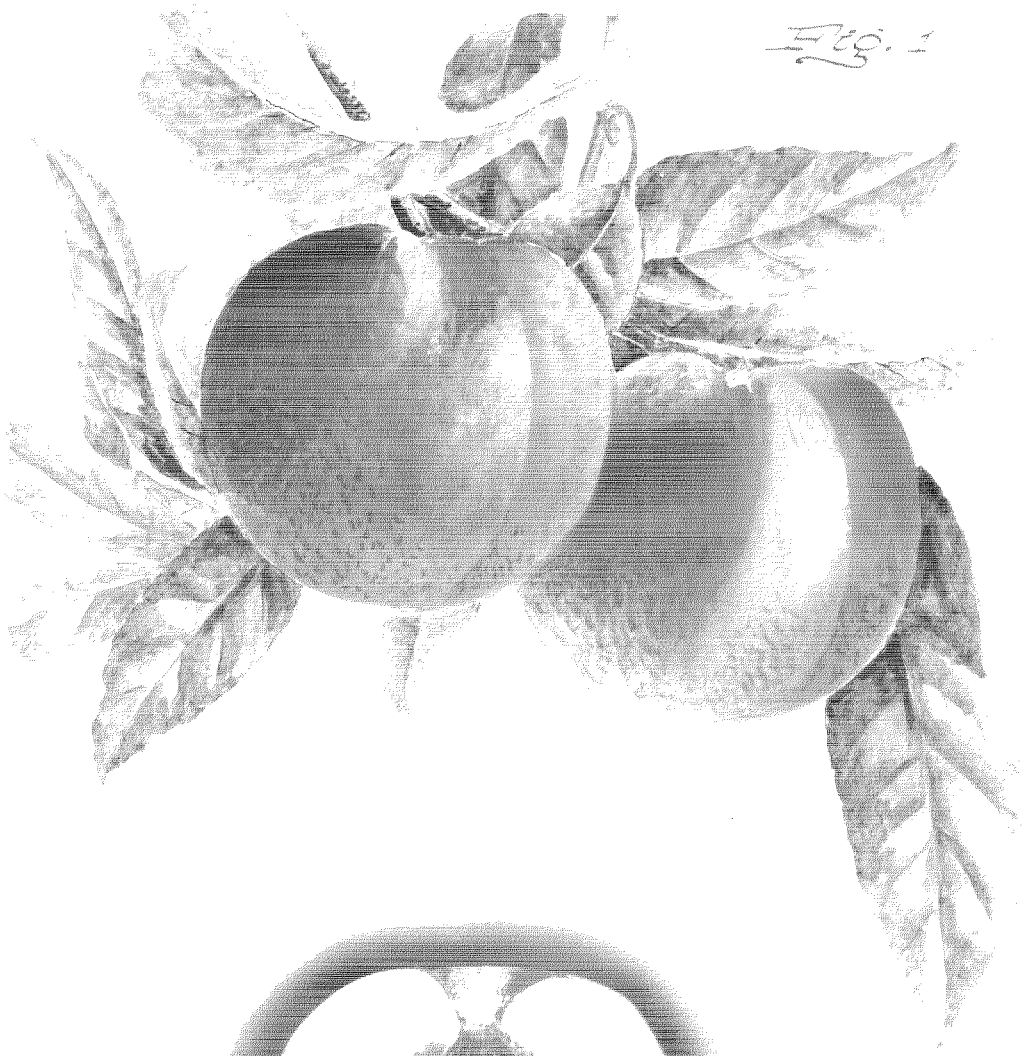
Fig. 1 is an elevation showing two of the fruit, together with a twig and leaves.
Figure 2:
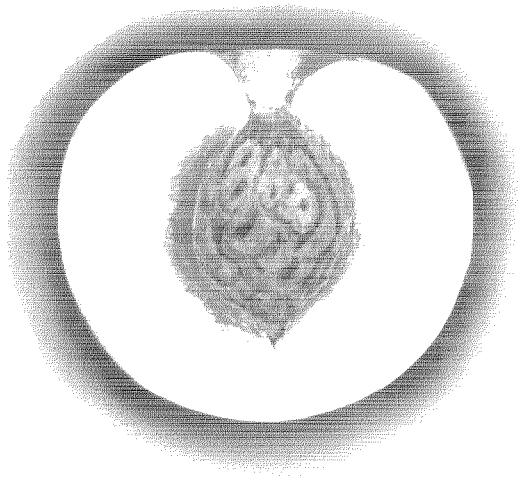
Fig. 2 is a sectional elevation of one of the fruit, with the stone remaining in place.

Referring now more specifically to the pomological details of this new and distinct variety of nectarine tree, the following is an outline description thereof; all major plate identifications being by reference to Maerz and Paul Dictionary of Color:

Tree:
- *Size.*—Large.
- *Vigor.*—Vigorous.
- *Production.*—Productive.

Trunk: Size—stocky.

Branches: Size—stocky to medium.

Leaves:
- *Size.*—Large to medium. Average length—6¼". Average width—1⅝".

- *Margin.*—Crenate.
- *Petiole.*—Medium length.
- *Glands.*—Average number—two to three on petiole; two to four on blade. Alternate; reniform. Stipules—none.
- *Color.*—Top side—medium green (22-L-6). Under side—lighter green (22-K-2).

Flower buds: Size—large to medium.

Flowers:
- *Date of first and full bloom.*—About with the Elberta peach (unpatented).
- *Size.*—Large—showy.

Fruit:
- *Maturity when described.*—Eating ripe—August 20, 1957.
- *Date of first picking.*—August 18, 1957.
- *Date of last picking.*—August 28, 1957.
- *Size.*—Large; uniform. Average diameter axially—2¾". Average transversely in suture plane—2¾".
- *Form.*—Uniform; globose.
- *Suture.*—Shallow, with slight depression beyond pistil point.
- *Ventral surface.*—Rounded.
- *Cavity.*—Rounded. Average depth—⅜". Average breadth—⅝".
- *Base.*—Rounded.
- *Apex.*—Short; depressed.

Skin:
- *Thickness.*—Medium.
- *Texture.*—Tough.
- *Tenacity.*—Tenacious to flesh.
- *Tendency to crack.*—None.
- *Down.*—Wanting.
- *Color.*—Yellow ground color (9-L-4), shading to an orange cast (9-K-9), partially overspread with red (4-L-7), mottled and striped with a brownish red (7-L-6).

Flesh:
- *Amygdalin.*—Moderate.
- *Texture.*—Firm; meaty.
- *Fibers.*—Few.
- *Ripens.*—Even.
- *Flavor.*—Sub-acid; delicate.
- *Aroma.*—Distinct.
- *Eating quality.*—Good to best.
- *Color.*—Yellow (9-K-6, shading to 9-L-7), with a whitish yellow cast (9-D-3) near but short of the cavity; the flesh immediately surrounding such cavity being a purplish red (4-K-6).

Stone:
- *Type.*—Free.
- *Size.*—Large to medium. Average length—1½". Average breadth—1¼". Average thickness—⅞".
- *Form.*—Oblong to oval.
- *Base.*—Oblique.
- *Hilum.*—Oval.
- *Apex.*—Acute.
- *Sides.*—Equal.
- *Surface.*—Irregularly furrowed near base; pitted throughout.
- *Ridges.*—Continuous; jagged.
- *Pits.*—Elongated.
- *Ventral edge.*—Thin.
- *Dorsal edge.*—Full, with broad groove.
- *Tendency to split.*—Moderate.
- *Color.*—Brown (7-C-12, shading to 7-E-12).

Keeping quality: Good.

Use: Market.

Shipping Quality: Good.

The tree and its fruit herein described may vary in slight detail due to climatic and soil conditions under which the variety may be grown.

The following is claimed:

A new and distinct variety of nectarine tree, as illustrated and described, which bears large, firm, yellow fleshed, freestone fruit wherein the skin is a yellow ground color overspread with red, mottled and striped with a deeper brownish red; the fruit being characterized—in comparison with the Freedom nectarine—by fruit having a ripening period which is ten days to two weeks later, and of larger size, firmer flesh, and longer keeping quality; and further characterized—in comparison with the Golden Grand nectarine—by fruit which is more uniform in size, of firmer flesh, and of better eating quality.

No references cited.